US00PP15952P3

(12) United States Plant Patent
Boeder

(10) Patent No.: US PP15,952 P3
(45) Date of Patent: Sep. 13, 2005

(54) ***CHRYSANTHEMUM* PLANT NAMED 'NIRVANA IMPROVED'**

(50) Latin Name: *Chrysanthemum morifolium*
Varietal Denomination: Nirvana Improved

(75) Inventor: Mark Roland Boeder, Den Haag (NL)

(73) Assignee: Cleangro, Ltd., Chichester (GB)

( * ) Notice: Subject to any disclaimer, the term of this patent is extended or adjusted under 35 U.S.C. 154(b) by 151 days.

(21) Appl. No.: 10/622,678

(22) Filed: Jul. 17, 2003

(65) Prior Publication Data

US 2004/0231021 P1 Nov. 18, 2004

Related U.S. Application Data

(60) Provisional application No. 60/396,824, filed on Jul. 17, 2002.

(51) Int. Cl.[7] ..... A01H 5/00
(52) U.S. Cl. ..... Plt./286
(58) Field of Search ..... Plt./286

(56) References Cited

U.S. PATENT DOCUMENTS

2003/0056261 P1 3/2003 Boeder ..... Plt./286

OTHER PUBLICATIONS

Pot *Chrysanthemum* Catalog 2002 from Van Zanten North America listing 'Machismo Time' variety. See pp. 7 and 9 (color photograph).

1998 Ficor Catalog listing *Chrysanthemum* variety 'Macho Time.' See pp. 4 and 13.

1999 Ficor Catalog listing *Chrysanthemum* variety 'Macho Time.' See pp. 4 and 13.

2000 Ficor Catalog listing *Chrysanthemum* variety 'Machismo Time.' See pp. 4 and 13.

2001 Ficor Catalog listing *Chrysanthemum* variety 'Machismo Time.' See pp. 4 and 9.

2002 Ficor Catalog listing *Chrysanthemum* variety 'Machismo Time.' See pp. 4 and 9.

*Primary Examiner*—Anne Marie Grunberg
*Assistant Examiner*—Annette H Para
(74) *Attorney, Agent, or Firm*—Howrey Simon Arnold & White, LLP

(57) ABSTRACT

A new variety of *Chrysanthemum* plant named 'Nirvana Improved,' having a good uniform canopy of large yellow and red single flowers with a green disc. The new variety has medium to tall vigor with a flat capitulum, free branching, uniform spreading habit and good foliage presentation.

1 Drawing Sheet

Latin name of the genus and species: Botanical classification: *Chrysanthemum morifolium.*

Variety denomination: The new *Chrysanthemum* variety denomination is 'Nirvana Improved.'

BACKGROUND OF THE INVENTION

The present invention comprises a new and distinct cultivar of *Chrysanthemum* botanically known as *Chrysanthemum morifolium*, and referred to by the cultivar name 'Nirvana Improved'.

'Nirvana Improved', identified as 20668-1, originated from a cross made in a controlled breeding program in Cleangro Limited, Vinnetrow Road, Chichester, West Sussex, United Kingdom. The female parent of the new variety is an undistributed, unpatented seedling identified as 'P452C7'. The male parent of the new variety is an undistributed, unpatented seedling identified as '20038-0'. The new variety 'Nirvana Improved' has been asexually reproduced by vegetative cuttings in Chichester, West Sussex, United Kingdom, and the distinguishing characteristics are retained through successive generations of asexual reproduction.

BRIEF SUMMARY OF THE INVENTION

'Nirvana Improved' is a pot type of *Chrysanthemum* plant variety having yellow and red single flowers with a light green disc.

Comparison with Female Parent

Plants of the new *Chrysanthemum* variety 'Nirvana Improved' are dissimilar to the female parent 'P452C7' in plant habitat and growth rate. In side-by-side comparisons in Chichester, West Sussex, United Kingdom, under commercial practice, plants of the new *Chrysanthemum* variety 'Nirvana Improved' differed from plants of the parent 'P452C7' in the following characteristics.

1. The new variety 'Nirvana Improved' produces yellow and red single flowers whereas the parent 'P452C7' produces white and purple flowers.
2. Plants of the new variety 'Nirvana Improved' have larger and taller inflorescence than plants of the parent 'P452C7'.

Comparison with Male Parent

Plants of the new *Chrysanthemum* variety 'Nirvana Improved' are dissimilar to the male parent '20038-0' in plant habitat and growth rate. In side-by-side comparisons in Chichester, West Sussex, United Kingdom, under commercial practice, plants of the new *Chrysanthemum* variety 'Nirvana Improved' differed from plants of the parent '20038-0' in the following characteristics.

1. The new variety 'Nirvana Improved' produces yellow and red single flowers whereas the parent '20038-0' produces red single flowers.

2. Plants of the new variety 'Nirvana Improved' have larger and taller inflorescence than plants of the parent '20038-0'.

Comparison with Other Varieties

Plants of the new *Chrysanthemum* variety 'Nirvana Improved' are similar to 'Machismo Time' (U.S. Plant patent application Publication No. US 2003/0056261) in plant habitat and growth rate. However, in side-by-side comparisons in Chichester, West Sussex, United Kingdom, under commercial practice, plants of the new *Chrysanthemum* variety 'Nirvana Improved' compared to plants of 'Machismo Time' in the following characteristics.

1. Plants of the new variety 'Nirvana Improved' have larger and taller inflorescence than plants of 'Machismo Time'.
2. The flowers of the new variety 'Nirvana Improved' have more yellow contrast than 'Machismo Time'.

BRIEF DESCRIPTION OF ILLUSTRATIONS

Typical specimens of the plant and flowers for the new *Chrysanthemum* variety 'Nirvana Improved' are shown in the accompanying digital photograph. The colors shown are as true as possible within the usual limits of this kind of illustration.

FIG. 1 is a whole plant view of the new variety 'Nirvana Improved' grown in a pot. The plant shown in the illustration and described here is 52 days from the commencement of Short Days.

DETAILED BOTANICAL DESCRIPTION

The following description of the new *Chrysanthemum* variety 'Nirvana Improved' is of plants grown in a greenhouse in Chichester, West Sussex, United Kingdom, in the month of February. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 18° C. at night and about 24° C. to 25° C. during the day under light conditions of about 5000 to 6000 foot candles. The plants respond well to the use of growth retardant, such as B9 treatment. To produce a commercial product the plants may be pinched once with the center bud removed. The typical container size for commercial growth is 14 cm. It has been observed that the shelf life of the new variety is about 24 days with a response time of about 7.5 weeks. The new variety is suitable for growth in a temperature range of 17° C. to 28° C.

The following description is with respect to a plant produced as pot *Chrysanthemum.* In the description of this new *Chrysanthemum* variety, color values have been taken from The Royal Horticultural Society Colour Chart (R.H.S.C.C.).

Plant

Plant type: Pot.
Habit: Upright and free branching.
Height: 21 cm.
Width: 36 cm.
Branching characteristics: Upright and free branching.
Length of lateral branches: 5–16 cm.
Diameter of lateral branches: 0.7 cm.
Texture of lateral branches: Slightly pubescent.
Number of breaks from pinch: 3–5.
Stem length: 5.5 cm.
Stem diameter: 0.6 cm.
Stem color: 137C.
Stem texture: Slightly pubescent.
Response time: 52.
Vigor: Medium/Tall.
Shelf life: 24 days.
Disease/pest (susceptibility/resistance observed): None observed to date.
Growth retardant type and treatment: 3 applications of 2.5 gm/liter B9 @ 2, 21 and 28 days after sticking of unrooted cuttings.

The plants were grown for 3 weeks in Long Day conditions (20 hours of light) and then transferred to Short Day conditions (13 hours of dark).

Propagation:
*Type.*—Vegetative Propagation Via Stem Cuttings.
*Time to rooting.*—12–14 days with soil temperatures of 18° C.
*Rooting habit.*—Fine and Fibrous.

Foliage

Number of leaves per lateral branch: 8–11.
Compound or single: Single.
Arrangement of leaves: Alternate.
*Shape of leaf.*—Typically 5 lobed ovate.
*Size of leaf.*—Width (cm): 5–8.5 cm. Length (cm): 3–10 cm.
*Leaf apex.*—Acute.
*Base.*—Cordate.
*Attachment.*—Petioled.
*Aspect.*—Slightly undulating.
*Margin.*—Palmetely lobed.
*Surface characteristics.*—Top: Slightly pubescent. Bottom: Pubescent.
Petiole:
*Color.*—139C.
*Length.*—0.5–2.5 cm.
*Diameter.*—0.2 cm.
*Texture.*—Slightly pubescent.
Venation: Net prominent midvein at underside.
*Color.*—Upper side: Near 138B. Under side: Near 138B.
Color:
*Mature leaf, upper side.*—Near 137A; under side: Near 137B.
*Young leaf, upper side.*—Near 137B; under side: Near 138A.

Flower

Flower appearance: Matte.
Flower type: Single.
Flower form: Flat.
Flower shape: Circular.
Flower habit: Flat Capitulum.
Number of blossoms per branch: 3–5.
Typical flowering season: January–December.
Inflorescence form: Cyme.
*Depth of fully expanded blossoms.*—1.5 cm.
*Diameter of fully expanded blossoms.*—9 cm.

Phyllaries:
*Number.*—25–30.
*Outer color.*—Near 137C.
*Length.*—0.5–0.9 cm.
*Width.*—0.2–0.5 cm.
*Texture/appearance.*—Pubescent.

Peduncle: Peduncle length is shortest at the terminal flower and progressively longer moving down the stem.
*Length.*—3–12 cm, average 5 cm.
*Color.*—Near 137D.
*Diameter.*—0.7 cm.
*Surface.*—Pubescent.
*Habit.*—Slightly curving.
*Strength.*—Moderately strong.

Pedicel:
*Length.*—Terminal: 3–6 cm; lateral 5–8 cm.
*Diameter.*—0.3 cm.
*Color.*—Near 139C.
*Surface.*—Pubescent.
*Habit.*—Slightly curving.
*Strength.*—Moderately strong.

Ray florets:
*Form/shape.*—Straight with parallel edges to the central mid-vein and a rounded tip.
*Texture/appearance.*—Matte.
*Number per flower.*—30.
*Length.*—2.5 cm.
*Width*—0.8 cm.
*Apex.*—Rounded.
*Base.*—Tapered.
*Margin.*—Entire.

Disc florets:
*Form/shape.*—Cylindrical.
*Texture/appearance.*—Shiny.
*Number per flower.*—150–200.
*Length.*—0.6 cm.
*Width:*—0.1 cm.
*Diameter of disc.*—1.5 cm.

Fragrance: None.

Flower bud (at onset of color):
*Length.*—0.5 cm.
*Diameter.*—1 cm.
*Form/shape.*—Globular.

General flower color:
1. *Ray florets, upper side.*—Immature: Near 44B from base to center and 16B from center to apex. Mature: Near 44B from base to center and 16C from center to apex. Older/Fading: Near 44C from base to center and 16C from center to apex.
2. *Ray florets, under side.*—Immature: Near 44B from base to center and 16C from center to apex. Mature: Near 44B from base to center and 16D from center to apex. Older/Fading: Near 44B from base to center and 16D from center to apex.
3. *Disc florets.*—Immature: Near 143C. Mature: Near 151B. Older/Fading: Near 151D.
4. *Bud.*—44C.

Flower progression with age: Flower form does not change but there is a slight fading of color.

Lastingness of blooms: About 24 days.

Reproductive Organs

Gynoecium: Observed on Ray and Disc florets.

Ray florets per individual flower:
*Pistil number.*—>25.
*Stigma color.*—Near 7A.
*Stigma shape.*—Forked.
*Style color.*—Near 145C.
*Style length.*—0.4 cm.

Disc florets per individual flower:
*Pistil number.*—>25.
*Stigma color.*—Near 7A.
*Stigma shape.*—Forked.
*Style color.*—Near 145C.
*Style length.*—0.4 cm.

Androecium: Not observed.

Fruit and seeds: None observed to date.

What is claimed is:

1. A new and distinct variety of *Chrysanthemum* plant, substantially as described and illustrated herein.

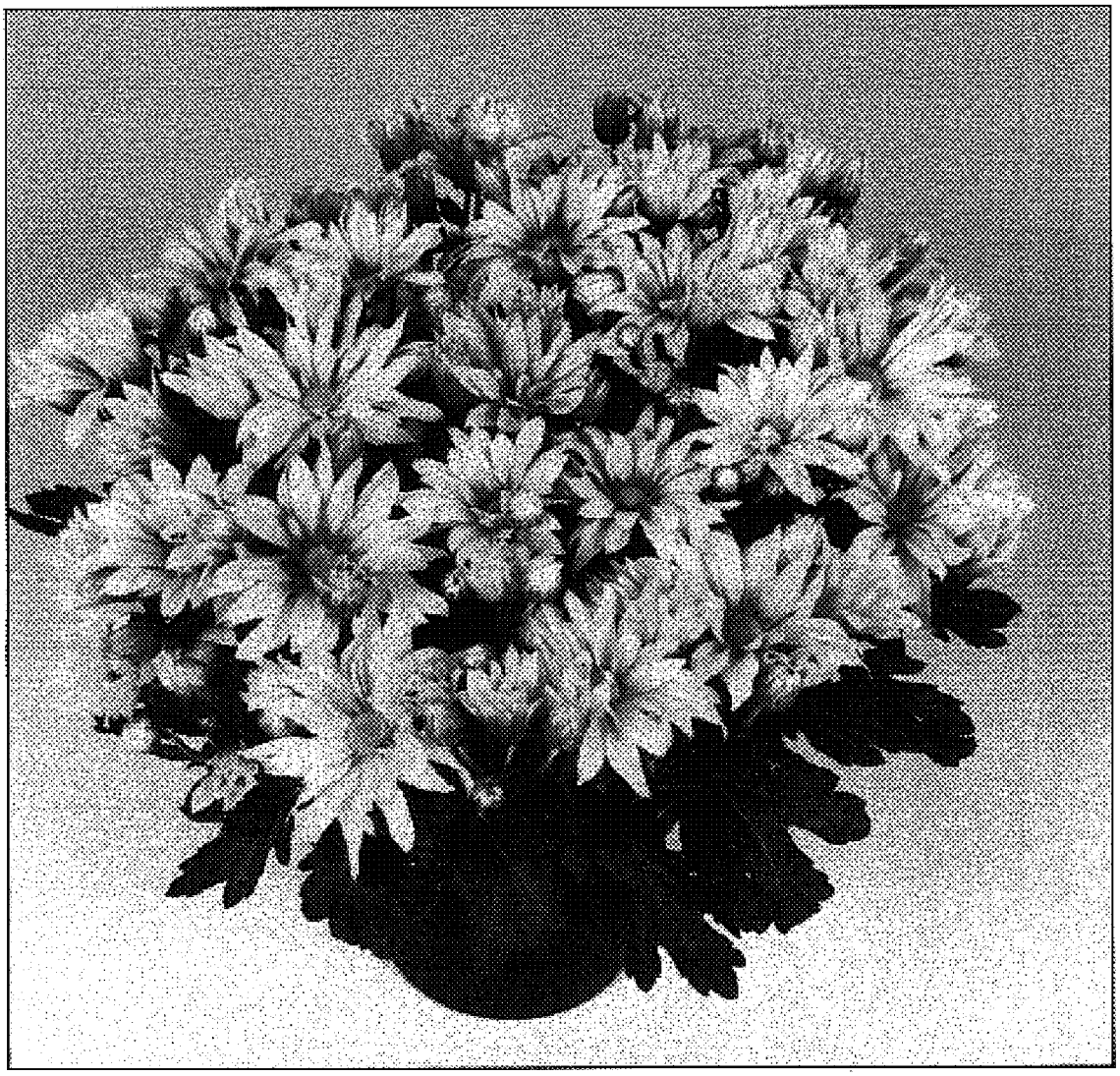

* * * * *